United States Patent [19]

Menschik

[11] 3,969,773

[45] July 20, 1976

[54] PROSTHETIC KNEE JOINT FOR ATTACHMENT TO A NATURAL OR PROSTHETIC LEG

[76] Inventor: Alfred Menschik, Donaueschingenstrasse 13,, A 1200 Vienna, Austria

[22] Filed: Aug. 22, 1974

[21] Appl. No.: 499,565

[30] Foreign Application Priority Data

Aug. 24, 1973  Austria .............................. 7405/73
July 8, 1974    Germany ........................... 2432766

[52] U.S. Cl. ...................................... 3/1.911; 3/22
[51] Int. Cl.² ...................... A61F 1/24; A61F 1/04; A61F 1/08
[58] Field of Search ................................ 3/22–29, 3/2, 1.9–1.911

[56] References Cited
UNITED STATES PATENTS

| 3,885,252 | 5/1975 | Nakajima | 3/22 X |
| R1,907 | 3/1865 | Parmelee | 3/29 X |

FOREIGN PATENTS OR APPLICATIONS

| 1,187,444 | 3/1959 | France | 3/22 |
| 1,008,446 | 5/1957 | Germany | 3/22 |
| 841,190 | 6/1952 | Germany | 3/22 |

*Primary Examiner*—Ronald L. Frinks
*Attorney, Agent, or Firm*—Karl F. Ross; Herbert Dubno

[57] ABSTRACT

A femur-engaging upper base and a tibia-engaging lower base of a prosthetic knee joint are positively interconnected by an inextensible and incompressible coupling mechanism allowing the two bases to swing vertically between two relative limiting positions about 135° apart, one of these limiting positions corresponding to a substantial alignment of the femur with the tibia. Throughout the swing, a more forwardly located first point (A) and a more rearwardly located second point (B) on the upper base are held at a substantially fixed distances from a more rearwardly located third point (D) and from a more forwardly located fourth point (C) on the lower base, respectively, these four points thus constituting the fulcra of a four-bar kinematic linkage. The coupling mechanism may be realized with a pair of intersecting rigid links hinged to the bases, arcuate guides in cheek plates for studs laterally projecting from the bases at the aforementioned four points, confronting projections on the bases rollingly engaging each other along curved ridges substantially conforming to the centrodes for the coupler motion of the four-bar linkage, or some combination thereof. Where crossed links are used, their hinges may be constructed as universal joints allowing limited relative rotation of the bases about an axis lying in the swing plane, such rotation being impeded by a link-engaging detent in the position of alignment between femur and tibia.

14 Claims, 14 Drawing Figures

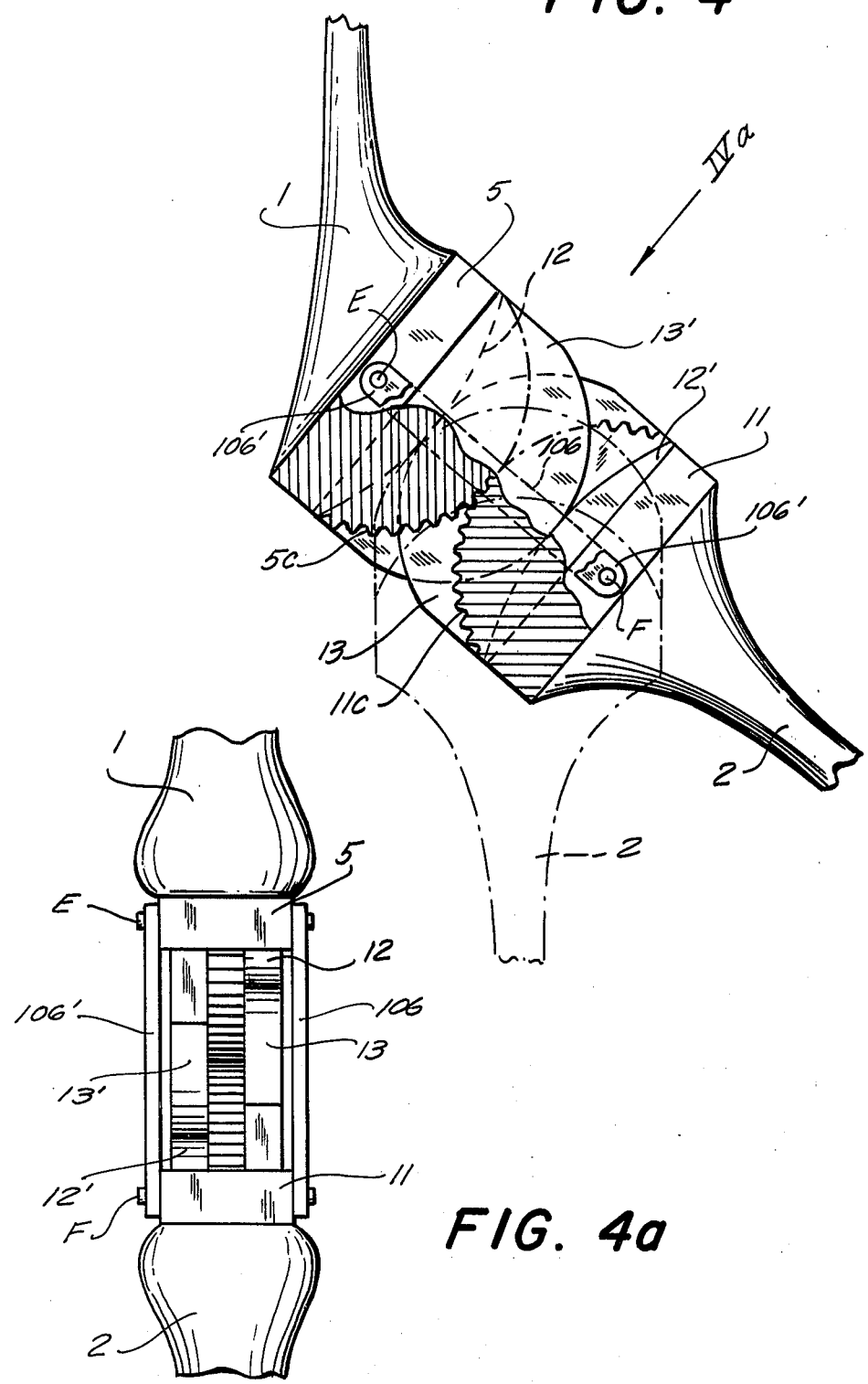

FIG. 6
FIG. 6c
FIG. 6a
FIG. 6b
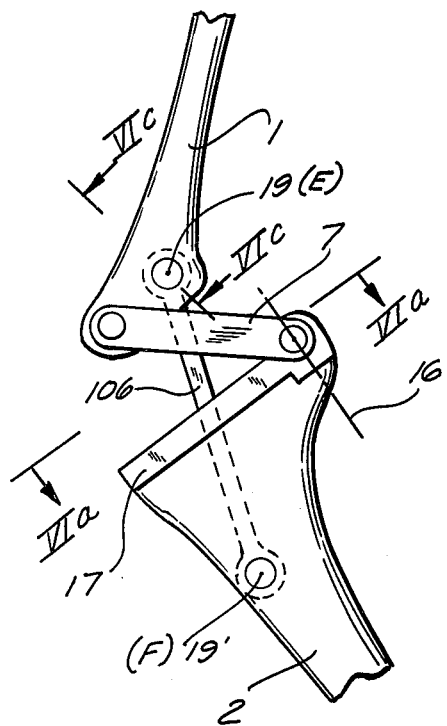
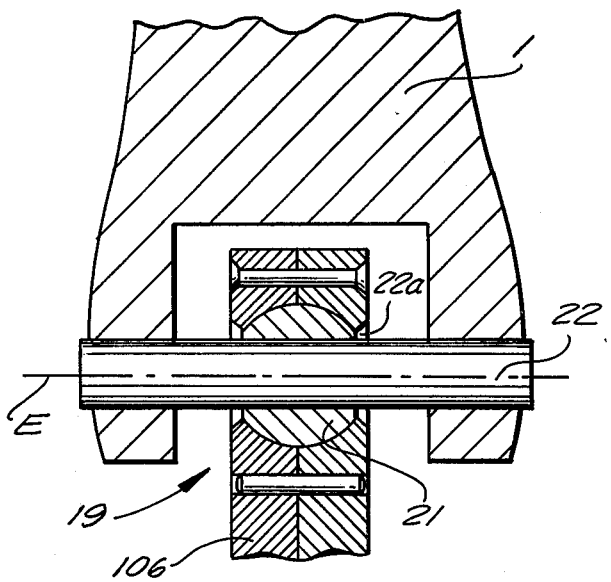
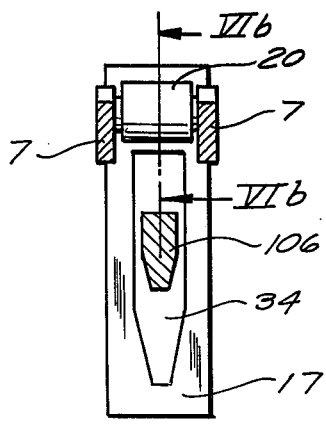
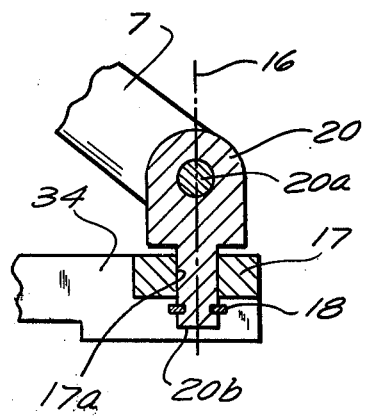

FIG. 7
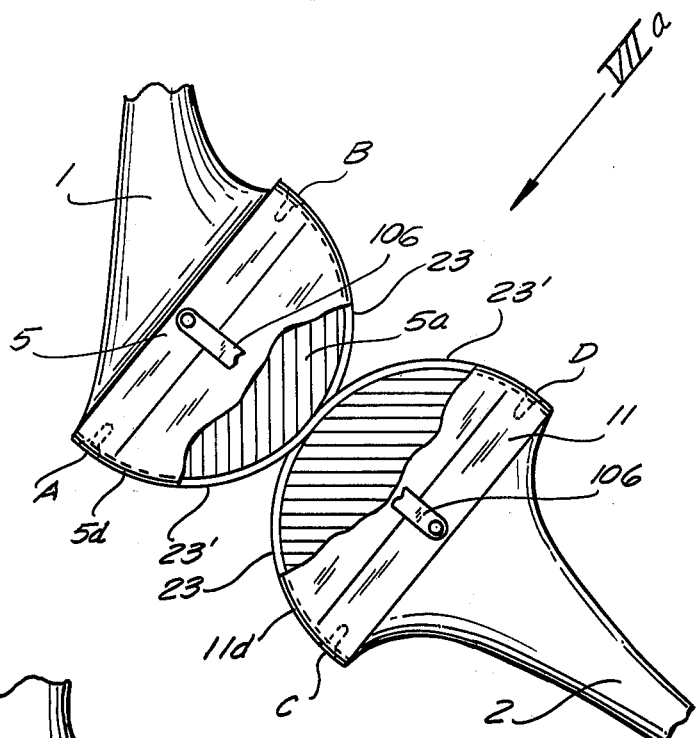
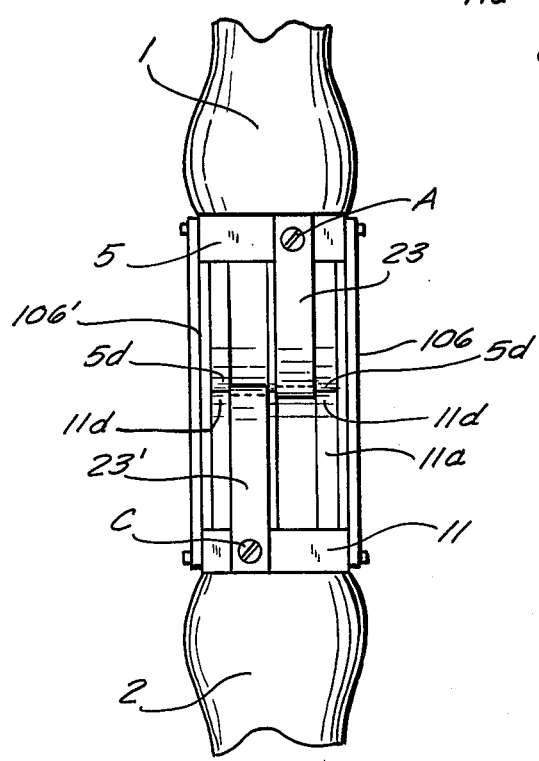
FIG. 7a

PROSTHETIC KNEE JOINT FOR ATTACHMENT TO A NATURAL OR PROSTHETIC LEG

FIELD OF THE INVENTION

My present invention relates to a prosthetic knee joint to be inserted between an upper leg portion, i.e. a femur or thigh, and a lower leg portion, i.e. a tibia or shank, with or without partial or complete replacement of either of these leg portions by a corresponding prosthesis.

BACKGROUND OF THE INVENTION

Many prosthetic joints are designed as simple hinges allowing the tibia to swing about a fixed fulcrum on the femur. This arrangement does not duplicate the natural motion of the human knee and is therefore inconvenient in cases where most of the tibia and the soft tissue around the knee, including muscles, veins and tendons, have remained intact. Even in a full prosthesis such a joint makes walking difficult, especially where the other leg functions normally.

It has already been proposed (see, for example, Austrian Pat. No. 212,973) to connect a tibia to a femur via a pair of extensible, spring-loaded intersecting links urging a convex ridge on the femur into contact with a concave track on the tibia. Since the ligaments of the natural knee joint are practically inextensible, being maintained in a taut state by the tissue surrounding the condyles, such a system also fails to reproduce the normal knee action.

In a somewhat similar system, described in German Pat. No. 841,190, the two leg portions are interconnected by a pair of rigid links which in a limiting forward position, conforming to a stretched leg, define with the associated mountings a four-bar kinematic linkage of substantially triangular configuration, i.e. with three of their four hinge points or fulcra approximately in line with one another. This, too, represents a substantial deviation from the natural joint.

OBJECTS OF THE INVENTION

It is, therefore, the general object of my present invention to provide an improved prosthetic knee joint whose function closely approaches that of the natural human knee.

Another object is to provide a prosthetic joint of this description which is of simple construction and dependable in operation, dispensing with fatigue-prone elements such as springs.

A more particular object is to provide means in such a joint for enabling limited relative rotation of the shank and the thigh about an axis lying in the vertical swing plane, at least in the bent position of the leg, in essentially the same way in which the natural knee permits the bent shank to turn on its own axis.

SUMMARY OF THE INVENTION

I realize the foregoing objects, in accordance with my present invention, by the provision of a femur-engaging upper base and a tibia-engaging lower base, positively interconnected by an inextensible and incompressible coupling mechanism which includes at least two rigid members, this mechanism facilitating a swinging of the lower base relative to the upper base in a vertical plane between a front limiting position and a rear limiting position; advantageously, the swing range between these two limiting positions extends over an arc greater than 90°, preferably up to about 135°. The construction of the coupling mechanism is such that the respective distances of a more forwardly located first point (A) and a more rearwardly located second point (B) on the upper base from a more rearwardly located third point (D) and a more forwardly located fourth point (C) on the lower base remain substantially constant on the swing range. These four points A, B, C and D can thus be regarded as the fulcra of a four-bar linkage, real or imaginary, with a fixed link defined by the points of one base (A and B) and a coupler defined by the points of the other base (e.g. C and D).

Since the natural knee joint has two crossing ligaments extending between the condyles, its operation is analogous to that of my improved prosthesis.

Thus, the coupling mechanism provided in a knee joint according to this invention may be constituted by a pair of rigid links respectively articulated to the two bases at points A, D and B, C. In an advantageous construction of this nature, the links of the quadrilateral are related to one another in a ratio of substantially 2:5:4:5 for the distances A–B, C–D, A–D and B–C. Such a construction also makes it possible, pursuant to a further feature of my invention, to join the links swingably to the two bases so as to enable limited relative rotation of these bases about an axis lying in the vertical swing plane, as noted above. To prevent such relative rotation in the front limiting position, in which the femur and the tibia are substantially in line with each other as determined by suitable stops, one base may be provided with detent means effective in that stretched position.

Generally, the relative orientation of the bases should be so chosen that the line A–B substantially parallels the line C–D in an intermediate position midway between the two limiting positions, thus allowing the shank to swing both forwardly and rearwardly from this intermediate position with a motion corresponding to the rolling of two approximately symmetrical convex surfaces on each other, these surfaces representing the fixed and the movable centrode for the coupler motion of the quadrilateral linkage if the preferably shorter line A–B is regarded as the fixed link and the line C–D is regarded as the coupler (or vice versa).

It will therefore also be possible to supplement or replace the action of the two crossing links by the interengagement of a pair of convex ridges in rolling contact with each other, these ridges being formed by two confronting projections respectively disposed on the upper and lower base. For a more positive interengagement of these rolling surfaces, the ridges may be provided with meshing teeth. Advantageously, in order to limit the depth of interpenetration of these teeth, the bases may also be formed with abutments in sliding contact with each other alongside the rollingly coacting projections.

Alternatively, rolling contact between these confronting surfaces can also be insured with the aid of a pair of flexible but substantially inextensible straps anchored to both bases, one strap extending from point A over a front portion of the upper ridge and a complementary rear portion of the lower ridge to point D, the other strap extending from point B over a rear portion of the upper ridge and a complementary front portion of the lower ridge to point C. Since these straps positively prevent any relative sliding of the coacting surfaces, the latter need not be toothed in that case.

Instead of the crossing links I may also provide four arcuate guide tracks, respectively centered on points A–D, on two or more cam plates mounted on the bases, the guide tracks of a cam plate or set of cam plates secured to one base being engaged by lateral studs on the other base in line with the associated articulation points. The studs are preferably provided with bearing means such as rollers or low-friction coatings.

BRIEF DESCRIPTION OF THE DRAWING

The above and other features of my invention will now be described in detail with reference to the accompanying drawing in which:

FIG. 4 is a side-elevational view (parts broken away) of a further embodiment;

FIG. 4a is a rear view of the joint of FIG. 4 as seen in the direction of arrow IVa;

FIG. 6 is a side-elevational view of yet a further embodiment;

FIG. 6a is a cross-sectional view taken on the line VIa — VIa of FIG. 6;

FIG. 6b is a cross-sectional view taken on the line VIb — VIb of FIG. 6a but drawn to a larger scale;

FIG. 6c is an enlarged cross-sectional view taken on the line VIc — VIc of FIG. 6;

FIG. 7 is a view similar to FIG. 4, illustrating a modification of the joint illustrated there; and FIG. 7a is a rear view of the joint of FIG. 7 as seen in the direction of arrow VIIa.

SPECIFIC DESCRIPTION

Figure 1:
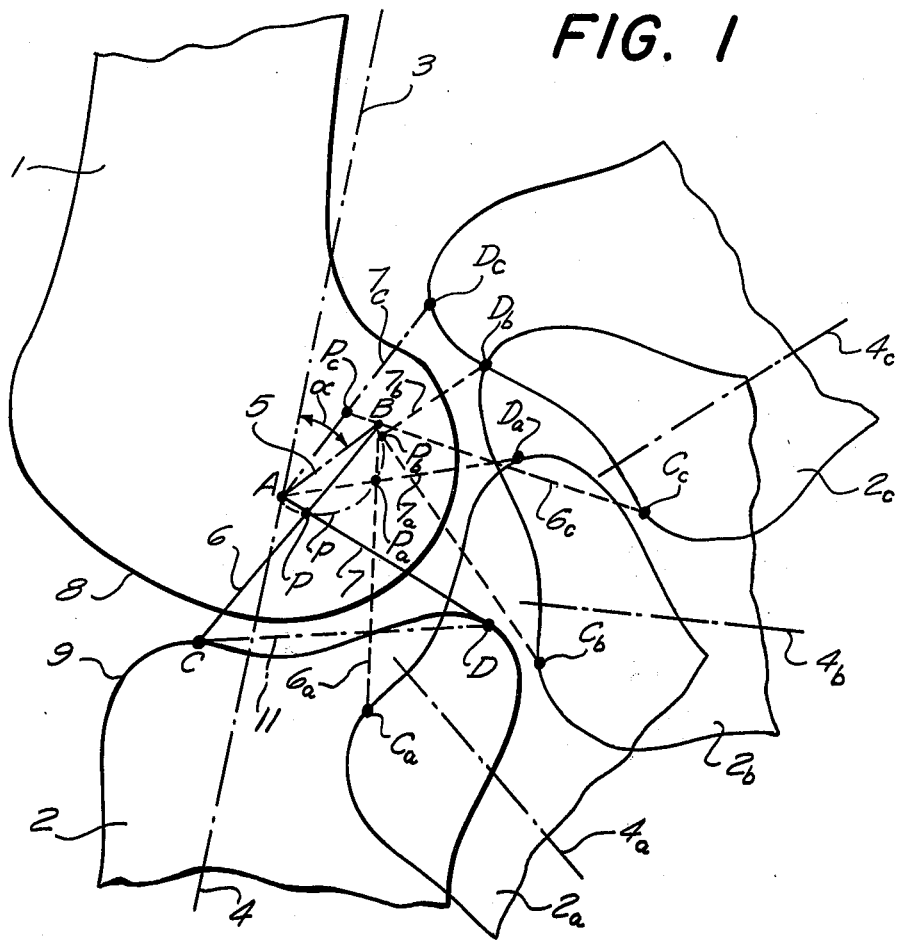
FIG. 1 is a schematic representation of the motion of a natural knee, with the femur at rest.

In FIG. 1 I have indicated at 1 the lower part of the femur of a human leg with its condyle 8 confronting the condyle 9 of the tibia 2 whose axis 4 is in line with the axis 3 of the femur. Two intersecting ligaments 6 and 7 extend from the upper condyle 8 to the lower condyle 9; ligament 7 is attached to condyle 8 at a forwardly located point A and to condyle 9 at a rearwardly located point D, ligament 6 being attached to condyle 8 at a rearwardly located point B and to condyle 9 at a forwardly located point C. Points A – D, at the ends of these intersecting ligaments, may thus be regarded as the fulcra of a four-bar kinematic linkage comprising a fixed link 5, spanning the points A and B, and a coupler 11, spanning the points C and D; link 5 includes with the common axis 3, 4 an angle $\alpha$ of approximately 40°. Ligaments 6 and 7 represent the cranks of this kinematic linkage.

The tibia 2 is rearwardly swingable from its aligned position, in a vertical plane, over a range of approximately 135° to another limiting position indicated at 2c, a pair of intermediate positions having been designated 2a and 2b. Analogously, the positions of axis 4, ligaments 6, 7 and anchor points C, D have been given the subscripts a, b and c in these alternate positions.

The linkage A–D retains its crossed-over character throughout most of the swing range, except in the vicinity of the rear limiting position where the ligaments no longer intersect as indicated at 6c and 7c. The fixed centrode $p$ for the motion of coupler 11 is a curve passing through the points of intersecton P, $P_1$, $P_b$, $P_c$ of link 7 with link 6 or with an extension thereof.

It will thus be seen that the tibia 2 does not rotate about a center in its swing plane and, furthermore, that the distance between the two condyles 8 and 9 remains substantially constant throughout the swing range. It will further be noted that the swing range of the two ligaments is substantially shorter than that of the tibia itself, amounting to about 110° for the ligament 6 and about 90° for the ligament 7. The contour of condyle 8 substantially parallels the centrode $p$ in the swing range but sharply deviates therefrom to the left of axis 3, 4 so that the tibia 2 may move only slightly beyond its illustrated aligned position in the forward direction, i.e. clockwise. Thus, centrode $p$ curves sharply toward point A beyond the intersection P which, in view of the acute angle $\alpha$, lies close to the fixed link 5.

In addition to the crossing ligaments 6 and 7, the natural knee joint further comprises a pair of lateral ligaments which are also substantially inextensible and whose position generally corresponds to that of a pair of links 106, 106' shown in FIGS. 4, 4a and 6.

I shall now describe with reference to the succeeding Figures a number of coupling mechanisms realizing the aforedescribed kinematic principles in a prosthetic knee joint according to my invention. In these following Figures I have used the same reference numerals as in FIG. 1 for corresponding elements, it being understood that numerals 1 and 2 may designate either natural thigh and shank bones or prosthetic substitutes therefor.

Figure 2A:
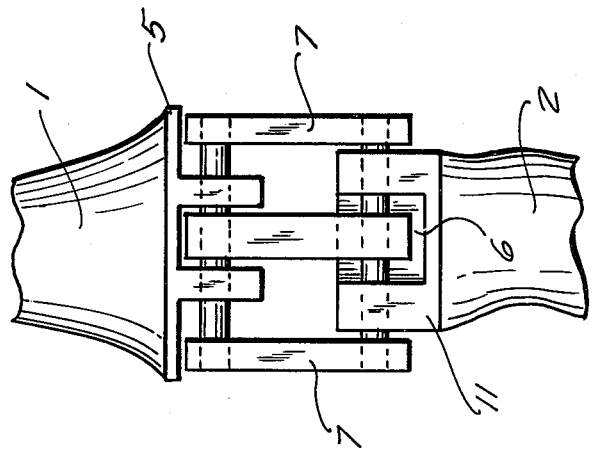
FIG. 2a is a rear view of the joint of FIG. 2 as seen in the direction of arrow IIa.
Figure 2:
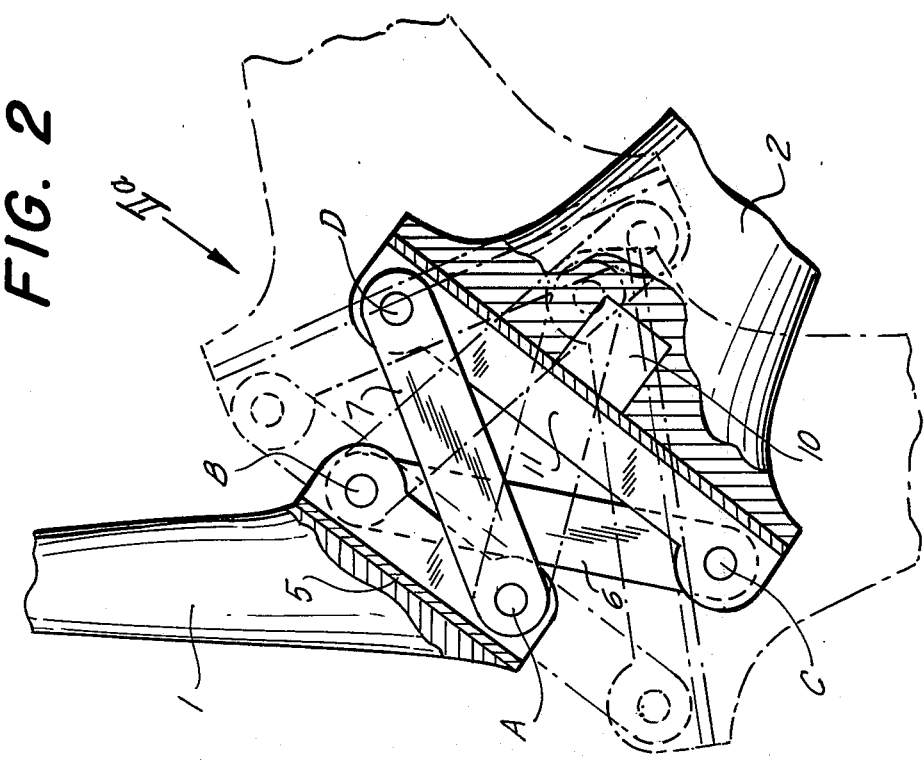
FIG. 2 is a side-elevational view, partly in section, of a prosthetic joint embodying my invention.

The system shown in FIGS. 2 and 2a comprises a pair of bases 5 and 11, respectively secured to femur 1 and tibia 2, which play the part of a fixed link and a coupler in conformity with the links so designated in FIG. 1. Bases 5 and 11 are essentially plate-shaped and can be secured to the associated natural or prosthetic leg portions 1 and 2 in a suitable manner, e.g. through a boss 10 as illustrated for the base 11.

Cranks 6 and 7 of the kinematic linkage A – D are represented in this embodiment by rigid arms respectively articulated to base 5 at B and A and to base 11 at C and D. In the illustrated position, the two bases and therefore the lines A – B and C – D are substantially parallel to each other; This is the approximate midposition of the swing range in which the tibia 2 includes an angle of roughly 60° with the femur 1. In its two limiting positions illustrated in phantom lines, the links come to rest against the underside of base plate 5 so that further motion is inhibited; it is of course desirable, in this and other instances, to let the tibia swing forwardly slightly beyond its position of alignment in order to improve the stability of the joint on standing.

Advantageous dimensions for the linkage of FIG. 2 are as follows:

| | |
|---|---|
| A - B | 22 mm |
| C - D | 50 mm |
| A - D | 42 mm |
| B - C | 50 mm |

This relationship satisfies Grashof's inequality for a drag linkage in which the two links 6 and 7 are theoretically able to make complete rotations; owing to the aforedescribed stops, however, only a fraction of a turn is utilized in the case of each crank.

Figure 3:
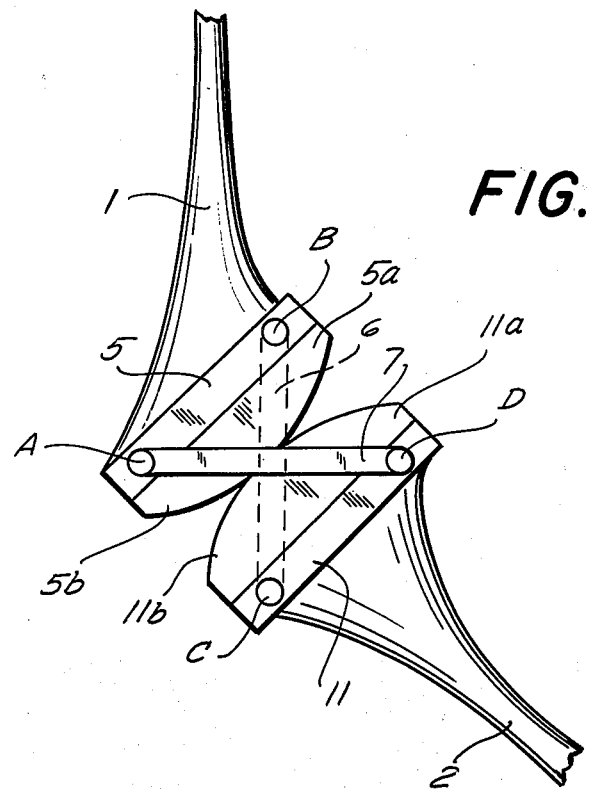
FIG. 3 is a side-elevational view of another prosthetic joint according to my invention.

As shown in FIG. 3, the bases 5 and 11 may be provided with confronting projections 5a and 11a whose convex ridges have been designated 5b and 11b and respectively conform to the fixed centrode and the movable centrode of the linkage A - D. The two ridges, therefore, roll on each other without sliding motion as the tibia 2 swings with reference to the femur 1.

The ridges 5b and 11b of projections 5a and 11a may be toothed for more positive interengagement. In that instance the links 6 and 7 could be omitted if other means are provided to keep their teeth in mesh with each other. This has been illustrated in FIGS. 4 and 4a where, however, the toothed ridge surfaces 5c and 11c are of semicircular shape, it being understood that only a central fraction of their arc length is utilized for the swing motion and that this fraction closely approximates the shape of the corresponding portions of curves 5b and 11b in FIG. 3. The centers of curvature E and F of ridges 5c and 11c, whose spacing from each other remains constant throughout the swing range, are interconnected by the aforementioned pair of rigid links 106 and 106' which generally correspond to the lateral ligaments of the natural knee. In order to relieve both these ligaments and the intermeshing teeth 5c and 11c from undue stress, I prefer to provide the two bases with lateral abutments 12, 13 and 12', 13' slidingly engaging each other. The working surfaces of abutments 13 and 13' can be circularly arcuate while those of abutments 12 and 12' may be generally flat.

Figure 5:
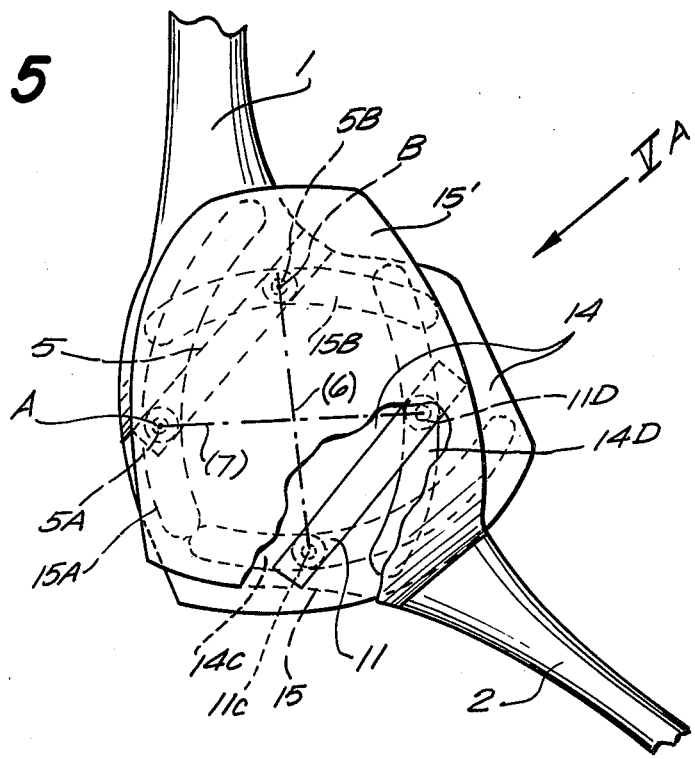
FIG. 5 is a side-elevational view of still another embodiment.
Figure 5A:
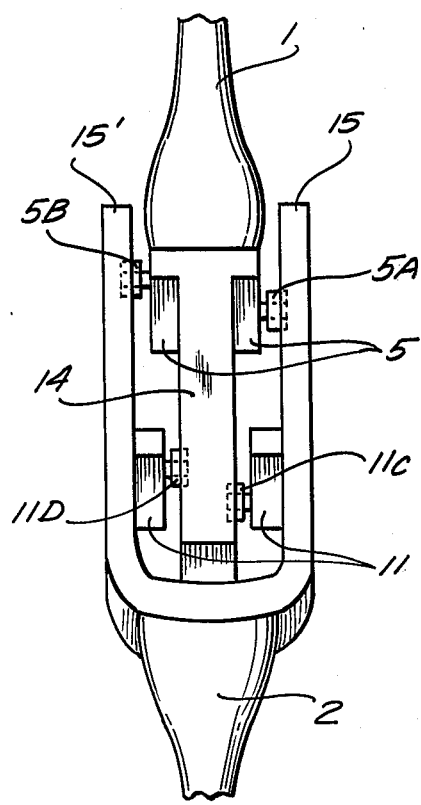
FIG. 5a is a rear view of the joint of FIG. 5 as seen in the direction of arrow Va.

FIGS. 5 and 5a show the possibility of replacing the crossing links 6, 7 of FIGS. 2 and 3 by cam plates 14 and 15, 15' respectively rigid with bases 5 and 11. Plate 14 is provided on opposite surfaces with a pair of guide grooves 14C and 14D which are respectively centered on points B and A of base 5 and are engaged by rollers 11C and 11D on base 11 in line with points C and D. Plates 15 and 15', flanking the plate 14, are provided with similar guide grooves 15A and 15B, respectively centered on points D and C, which are engaged by rollers 5A and 5B on base 5 in line with points A and B. It will be apparent that the mechanism of FIGS. 5 and 5a guides the tibia 2 with reference to the femur 1 in precisely the same manner as do the crossing links 6 and 7 of FIGS. 2 and 3, whose positions have been diagrammatically indicated in FIG. 5 at (6) and (7), and in approximately the same way as the joint of FIGS. 4 and 4a.

It is possible to replace the two plates 15 and 15' by a single plate, carrying both grooves 15A and 15B, and similarly to provide the two grooves 14C and 14D on one surface of plate 14 confronting the grooved surface of this single plate. In that case, however, the rollers 5A, 5B and 11C and 11D should be replaced by arcuate slides in order to prevent them from entering the wrong grooves at the points of intersection. The grooves of plates 15 and 15', or those of both plates in the two-plate modification just described, may be replaced by throughgoing slots.

In view of the fact that the lateral ligaments of the natural knee are virtually inextensible like the crossing ligaments, as noted above, it is possible to replace one of the intersecting links in the system of FIG. 2 (e.g. the link 6) by a somewhat longer link 106 (similar to that shown in FIGS. 4 and 4a) intersecting the other link (7) at a more acute angle. This has been illustrated in FIG. 6 where hinges 19 and 19', articulating the link 106 to the femur 1 and to the tibia 2, coincide with the points E and F of FIGS. 4 and 4a. In this prosthetic joint the link 106 passes through a slot 34 of a bracket 17 replacing the plate-shaped base 11 of the preceding embodiments, slot 34 converging forwardly so as to form a detent for the link 106 which has a matingly tapering cross-section as seen in FIG. 6a. The upper base, shown at 5 in the preceding Figures, is here represented by a bifurcate lower extremity of femur 1 as best seen in FIG. 6c. Hinge joint 19 comprises a transverse pin 22 carrying a ball 21 on which the link 106 is universally jointed; its lateral excursions out of the vertical swing plane, however, are limited by restricted frustoconical apertures 22a traversed by the pin 22. Hinge joint 19', by which the link 106 is articulated to tibia 2, is similar to hinge joint 19 and has therefore not been illustrated in detail.

Link 7, comprising a pair of parallel arms as in the embodiments of FIGS. 2 and 2a, is swivelably secured to lower base 17 so as to be limitedly rotatable about an axis 16 lying in the vertical swing plane. The arms 7 are interconnected by a pin 20a traversing the head of a bolt 20 whose shank 20b passes through a hole 17a in base 17 and is held in place by a jump ring 18. Joint 19' may be considered part of the lower base.

In the intermediate position illustrated in FIGS. 6 and 6a, and throughout the greater part of the swing range, link 106 is received in slot 34 with enough lateral clearance to enable the base 17, and therefore the tibia 2 integral therewith, to rotate also about the axis 16 with reference to the femur 1. In the front limiting position of the prosthetic joint, in which the link 106 is closely embraced by the narrowing slot 34, such rotation is no longer possible and the leg is stiffened against lateral buckling.

The aforedescribed rotation about axis 16 would also be possible if the lower hinge joint 19' were designed as an arcuately curved pin, centered on that axis, slidably embraced by an eye on the lower extremity of link 106. The preferred construction with a universal joint of the type shown in FIG. 6c is, however, considerably simpler.

FIGS. 7 and 7a show a modification of the system of FIGS. 4 and 4a, with omission of teeth 5c and 11c on projections 5a and 11a. These projections, which are now smooth-surface, are embraced by two S-shaped flexible but inextensible straps 23 and 23' passing over their surfaces in opposite direction. Strap 23' is fastened to base 5 at point A, hugs a forward part of the convex surface of projection 5a, then hugs a complementary rear part of projection 11a and terminates at point D where it is attached to base 11. Strap 23 is attached to base 5 at point B, hugs a rear portion of the surface of projection 5a and passes over a complementary front portion of the surface of projection 11a before engaging the base 11 at point C. The two straps are flanked by peripheral ribs 5d and 11d of projections 5 and 11 in contact with each other.

The operation of the system of FIGS. 7 and 7a is practically identical with that of the embodiment of FIGS. 4 and 4a.

I claim:

1. A prosthetic knee joint comprising:
   a femur-engaging upper base;
   a tibia-engaging lower base; and
   an inextensible and incompressible coupling including at least two rigid members positively interconnecting said bases, said coupling facilitating a swinging of said lower base relative to said upper base in a vertical plane between a front limiting position and a rear limiting position, the respective distances of a more forwardly located first point A and a more rearwardly located second point B on said upper base from a more rearwardly located third point D and from a more forwardly located fourth point C on said lower base being substantially constant throughout the swing range; the distance A–B of said first and second points, the distance C–D of said third and fourth points, the distance A–D of said first and third points, and the distance B–C of said second and fourth points being interrelated in a ratio of substantially 2:5:4:5.

2. A knee joint as defined in claim 1 wherein said swing range extends over an arc greater than 90°.

3. A knee joint as defined in claim 1 wherein said members include a first link articulated to said bases at said first and third points and a second link articulated to said bases at said second and fourth points.

4. A knee joint as defined in claim 3 wherein the spacing of said first and second points is less than that of said third and fourth points.

5. A knee joint as defined in claim 1 wherein said distance A–B is about 22 mm, said distance C–D is about 50 mm, said distance A–D is about 42 mm and said distance B–C is about 50 mm.

6. A knee joint as defined in claim 3 wherein said links are swivelably joined to said bases for enabling limited relative rotation thereof about an axis lying is said vertical plane.

7. A knee joint as defined in claim 6 wherein one of said bases is provided with detent means engageable with one of said links in said front limiting position for preventing said relative rotation.

8. A knee joint as defined in claim 7 wherein said detent means comprises a slotted bracket on said lower base straddling said second link.

9. a knee joint as defined in claim 1 wherein the line interconnecting said first and second points substantially parallels the line interconnecting said third and fourth points in an intermediate position midway between said limiting positions.

10. A knee joint as defined in claim 1 wherein said members include two confronting projections on said bases rollingly contacting each other along convex upper and lower ridges substantially curved along the fixed and movable centrodes for the coupler motion of a four-bar linkage with a fixed link defined by said first and second points A and B, a coupler defined by said third and fourth points D and C, and a pair of cranks respectively defined by said first and third points A and D and by said second and fourth points B and C.

11. A knee joint as defined in claim 10 wherein said ridges are provided with interengaging teeth.

12. A knee joint as defined in claim 11, further comprising coacting abutment means on said bases alongside said projections in sliding contact with each other for limiting interpenetration of said teeth.

13. A knee joint as defined in claim 10 wherein said coupling further comprises a pair of flexible but substantially inextensible straps each anchored to both said bases, one of said straps extending from said first point over a front portion of said upper ridge and a complementary rear portion of said lower ridge to said third point, the other of said straps extending from said second point over a rear portion of said upper ridge and a complementary front portion of said lower ridge to said fourth point.

14. A knee joint as defined in claim 1 wherein said members comprise first cam means rigid with said upper base, laterally overlying said lower base, and second cam means rigid with said lower base, laterally overlying said upper base, said first cam means being provided with first and second arcuate guide tracks respectively centered on said first and second points, said second cam means being provided with third and fourth arcuate guide tracks respectively centered on said third and fourth points, said upper base having a pair of laterally projecting studs in line with said first and second points respectively engaging said third and fourth guide tracks, said lower base having a pair of laterally projecting studs in line with said third and fourth points respectively engaging said first and second guide tracks.

* * * * *